United States Patent [19]
Silverstein

[11] Patent Number: 6,120,484
[45] Date of Patent: Sep. 19, 2000

[54] OTOLOGICAL IMPLANT FOR DELIVERY OF MEDICAMENT AND METHOD OF USING SAME

[76] Inventor: Herbert Silverstein, 1317 Vista Dr., Sarasota, Fla. 34239

[21] Appl. No.: 09/287,344

[22] Filed: Apr. 7, 1999

Related U.S. Application Data

[60] Provisional application No. 60/120,327, Feb. 17, 1999.

[51] Int. Cl.[7] .................................................. A61M 31/00
[52] U.S. Cl. .............................. 604/264; 424/427; 623/11
[58] Field of Search ........................... 604/264, 21, 164, 604/500, 501, 506; 424/427, 422, 437; 623/11, 12, 66

[56] References Cited

U.S. PATENT DOCUMENTS

| | | | |
|---|---|---|---|
| 2,642,065 | 6/1953 | Negri | 128/269 |
| 3,807,409 | 4/1974 | Paparella et al. | 128/350 |
| 3,865,108 | 2/1975 | Hartop | 128/260 |
| 3,871,380 | 3/1975 | Heros | 128/350 |
| 3,916,873 | 11/1975 | Wasserman | 128/1 R |
| 3,976,081 | 8/1976 | Lapidot | 128/350 |
| 4,034,759 | 7/1977 | Haerr | 128/260 |
| 4,094,303 | 6/1978 | Johnston | 128/1 R |
| 4,096,230 | 6/1978 | Haerr | 264/321 |
| 4,159,719 | 7/1979 | Haerr | 128/260 |
| 4,168,697 | 9/1979 | Cantekin | 128/1 R |
| 4,206,757 | 6/1980 | Grandadam et al. | 128/260 |
| 4,326,512 | 4/1982 | Peerless | 128/151 |
| 4,468,218 | 8/1984 | Armstrong | 604/49 |
| 4,568,337 | 2/1986 | Treharne, III et al. | 604/247 |
| 4,650,488 | 3/1987 | Bays et al. | 623/12 |
| 4,744,792 | 5/1988 | Sander et al. | 623/10 |
| 5,350,580 | 9/1994 | Muchow et al. | 424/437 |
| 5,421,818 | 6/1995 | Arenberg | 604/21 |
| 5,474,529 | 12/1995 | Arenberg | 604/21 |
| 5,476,446 | 12/1995 | Arenburg | 604/21 |
| 5,503,848 | 4/1996 | Perbellini et al. | 424/488 |
| 5,702,716 | 12/1997 | Dunn et al. | 424/422 |

OTHER PUBLICATIONS

L. Duberstein, "Intraluminal Tube Wick," Otolaryngology–Head and Neck Surgery, vol. 94, No. 1, Jan. 1986, pp. 135–136.

Commercial brochure from Americal Corporation for "Duberstein Intralumenal Tube Wick," publication date believed to be prior to 1999.

*Primary Examiner*—John B. Yasko
*Attorney, Agent, or Firm*—Pennie & Edmonds LLP

[57] ABSTRACT

The present invention is directed to an otological implant for delivery of medicament and a method of using the implant. The implant includes a wick inserted through an aperture in a membrane. One end of the wick is in contact with the treatment site and the other end is readily accessible. The wick is made of a material that will convey medication from one end of the wick to the other end of the wick by capillary action so that the medication is delivered to the treatment site. The implant may also include a tube member for supporting the wick. In use, the tube member is inserted in the membrane aperture and the wick is inserted in the lumen of the tube.

13 Claims, 3 Drawing Sheets

OTOLOGICAL IMPLANT FOR DELIVERY OF MEDICAMENT AND METHOD OF USING SAME

CROSS-REFERENCE TO RELATED APPLICATIONS

This is a continuation-in-part of U.S. Provisional Application No. 60/120,327, filed Feb. 17, 1999.

FIELD OF THE INVENTION

The present invention relates to a device and method for treating inner ear disease, and in particular to an otological implant and method for delivery of medicament.

BACKGROUND OF THE INVENTION

The clinical management of inner ear diseases such as vertigo of Meniere's disease, sudden viral deafness, and autoimmune allergic inner ear disease remains a challenge in otolaryngology. Although some diseases can be treated with systemic medications, not all diseases and patients are responsive to this treatment. Furthermore, relatively high concentrations of the medication are required with systemic treatment, regardless of whether the medication is administered intramuscularly, intravenously, or orally. Finally, some medications have undesirable systemic effects.

Direct treatment of inner ear diseases is an alternative to systemic medications.

Currently, there are several procedures available to deliver medication to the inner ear. In one procedure, a physician injects medication into the middle ear over the round window area through the tympanic membrane. The patient is asked not to swallow and must remain relatively still in the supine position with the head turned both during the injection and for some time afterwards (at least 30 minutes) to allow the medication to diffuse through the round window. A tube could be placed in the ear drum to convey medication. As there is no pathway for evacuation of air as the medication is applied through the tube, it is difficult to get the medication to go into the middle ear. This is analogous to a situation in which one attempts to pour fluid into a container that has only one hole. If the medication does not get into the middle ear, it may flow down the eustachian tube or it may not get directly to the round window membrane. In fact, most medication is lost down the eustachian tube when the patient swallows. Another drawback to this procedure is the need for repeated doctor visits for injection of the medicament. As a result, this procedure is not very cost or time efficient.

One technique for direct treatment that has been developed uses a small gelatin sponge placed on the round window membrane. The physician then injects the medication directly onto the sponge. Like direct treatment with a tube, this procedure requires many office visits and medicament may be lost down the eustachian tube. Furthermore, the gelatin material that the sponge is made of may deteriorate.

Another recently developed technique utilizes an indwelling catheter that requires an operating room surgical procedure for implantation. A micro-pump can be attached to the catheter to deliver exact amounts of medication. Although this technique has had some clinical success, the catheter, micro-pump, surgical procedure, and subsequent hospitalization are very expensive.

As the discussion above illustrates, there is a need for an improved method and device for treating inner ear diseases.

SUMMARY OF THE INVENTION

The present invention relates to an otological implant for delivery of medicament from a first side of a membrane to a treatment site located of a second side of the membrane. The implant has a wick with a distal end for contacting the treatment site, a proximal end for contacting a medicament source, and a body therebetween configured and dimensioned to pass through an aperture in the membrane. The wick is made of a material capable of conveying the medicament from the proximal end to the distal end by capillary action. One such material is polyvinyl acetate. Although the size and shape of the wick can be varied for different applications, preferably the wick has a substantially cylindrical shape.

The implant may also include a tube member for supporting the wick. The tube member is configured and dimensioned to fit in the membrane aperture and has a first end for positioning on the first side of the membrane, a second end for positioning on the second side of the membrane, and a body therebetween. The tube member body has a lumen sized to receive the wick. The tube may be made of titanium, a titanium alloy, stainless steel, nylon, or silicone, and is preferably shorter in length than the wick.

The tube member may have a flange on either or both ends for preventing movement of the tube in the aperture. The flanges may be oriented at a non-orthogonal angle with respect to the tube member body and the flange on the first end may have a tab to facilitate removal. In order to facilitate proper placement in the aperture, the tube member body may have a concave exterior surface.

The present invention also relates to a method for treatment of inner ear disease. The method includes the steps of creating an aperture in an ear drum; inserting a wick through the aperture with a first end of the wick located lateral to the ear drum and a second end of the wick located medial to the ear drum and in contact with a treatment site; and contacting the first end of the wick to a medicament source to allow the medicament to travel to the second end of the wick and thereby deliver medicament to the treatment site.

The method may also include the step of inserting a tube member in the aperture prior to inserting the wick as well as the step of removing obstructions around the treatment site prior to insertion of the wick. Preferably, the aperture in the ear drum is created using a laser or a myringotomy knife and an operating microscope is used to visualize the method.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
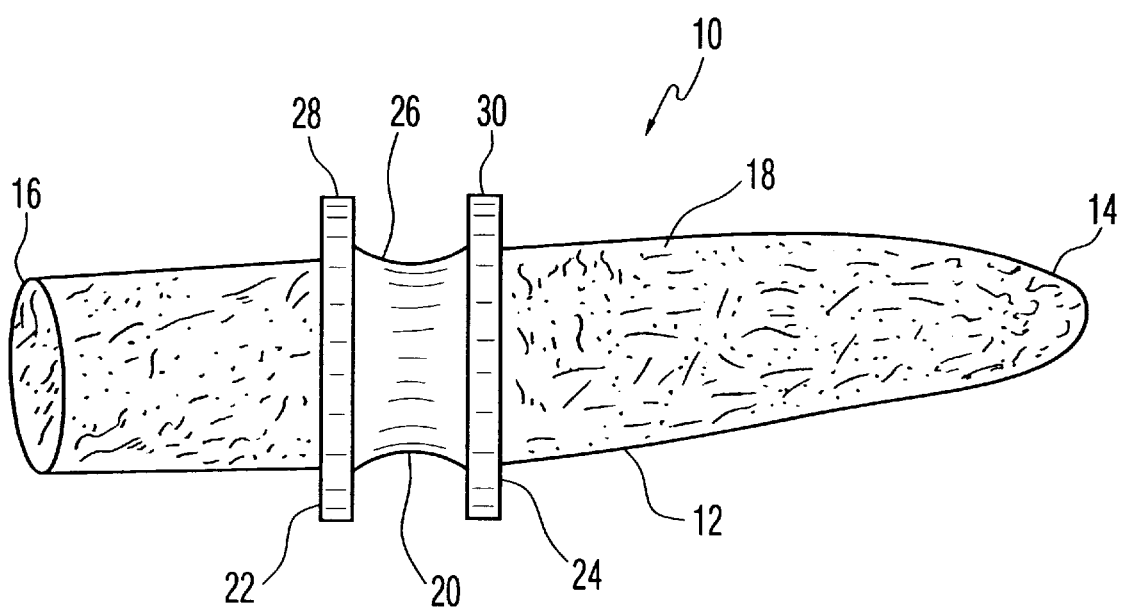
FIG. 1 shows a side view of one embodiment of the implant according to the present invention having a wick and a tube member.

FIG. 1 shows an otological implant 10 according to the present invention. One use of implant 10 is for delivery of medicament from one side of a membrane, such as the ear drum, to a treatment site located on the other side of the membrane. Implant 10 includes a wick 12 having a distal end 14, a proximal end 16, and a body 18 therebetween. Body 18 is sized to fit in an aperture in the membrane. Wick 12 is made of a material that is capable of conveying the medication from proximal end 16 to distal end 14 by capillary action. As described in more detail below, distal end 14 is in contact with the treatment site so that when proximal end 16 is in contact with the medication, the medication travels to proximal end 16 and thereby delivered to the treatment site. Wick 12 can have any suitable shape as long as body 18 has a portion that can fit through an aperture in the membrane. Preferably, wick 12 has a substantially cylindrical shape. Wick 12 can have a taper from proximal end 16 to distal end 14 so that the delivery of the medication to the treatment site can be more localized. The dimensions of wick 12 can be selected to suit a particular clinical situation. If wick 12 is substantially cylindrical, wick 12 preferably has a diameter of about 1 mm and a length of about 9 mm.

Although wick 12 can be made of any material that conveys a fluid under capillary action, wick 12 is preferably made of a pharmaceutically acceptable plastic material. Preferably, the wick is made of polyvinyl acetate (PVA) because this material has been used extensively in the ear, nose, and throat (ENT) specialty as an ear or nasal packing after surgery or to stop a bleeding nose. More importantly, PVA is well tolerated and has regulatory approval for implantation against mucus membranes for periods of up to four weeks.

Implant 10 also includes a tube member 20 which acts a grommet when inserted in the membrane aperture. Thus, wick 12 is passed through tube 20. Tube 20 can be made of any number of different biocompatible materials including metals such as titanium and stainless steel, plastics such as nylon or specialty materials such as silicones. After implantation, a first end 22 of tube 20 is on one side of the membrane, a second end 24 is on the other side, and a body 26 extends through the membrane aperture. Tube 20 has a lumen sized to receive wick 12. The diameter of wick 12 is smaller than the diameter of the lumen of tube 20 so that wick 12 can be easily inserted into tube 20. The smaller diameter of wick 12 also allows visualization of the other side of the membrane so that distal end 14 of wick 12 can be properly placed against the treatment site. Because wick 12 is made of a material that allows capillary action, wick 12 swells upon saturation with fluid. As a result, the diameter of wick 12 increases to press against the lumen of tube 20 and inhibit relative movement between wick 12 and tube 20.

In order to prevent tube 20 from dislodged from the membrane, first end 22 is provided with a flange 28 and second end 24 is also provided with a flange 30. Flanges 28, 30 rest against the membrane to prevent excessive insertion and unintended explantation, respectively. In this regard, flange 30 preferably has some elasticity (as would be the case if flange 30 is made of silicone) so that when tube 20 is intentionally pulled out of the membrane aperture after the treatment has ended, flange 30 bends back to allow flange 30 to pass through the aperture. Tube body 26 has a concave surface to facilitate proper seating of tube 20 in the aperture. The lumen can have a corresponding convex surface to assist in securing wick 12 to tube 20.

It should be noted that many different tube configurations can be used in implant 10.

Figure 2A:
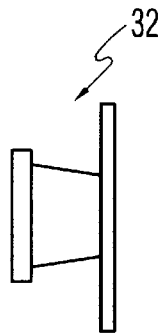
FIG. 2a through FIG. 2h show various embodiments of the tube member that can be used to support the wick.
Figure 2B:
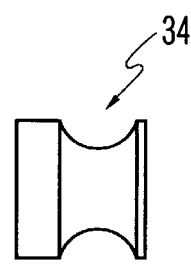
Figure 2C:
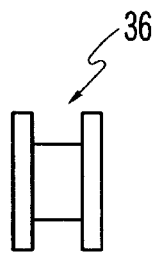
Figure 2D:
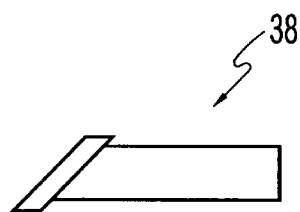
Figure 2E:
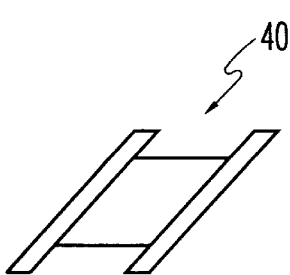
Figure 2F:
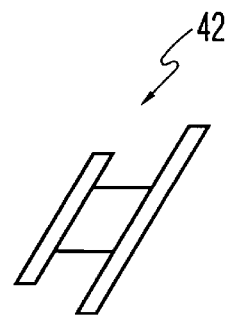
Figure 2G:
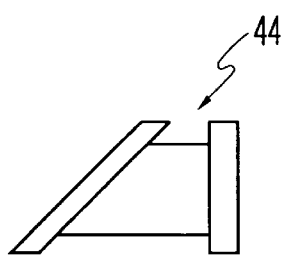
Figure 2H:
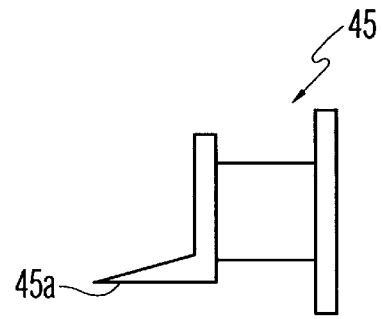

For example, different flange sizes and shapes are well known in the art. FIGS. 2a–2h show some example of suitable tube designs. Specifically, FIG. 2a shows a V-T tube 32 in which one flange is larger than the other flange and the tube body tapers toward one end. FIG. 2b shows a Shepard grommet 34 in which one flange is wider than the other. FIG. 2c shows a Donaldson type grommet 36 in which the tube body is cylindrical. FIG. 2d shows a shank style tube 38 having only one flange at a non-orthogonal orientation with respect to the tube body. FIG. 2e shows a grommet 40 having two flanges at a non-orthogonal orientation with respect to the tube body. FIG. 2f shows a grommet 42 also having two non-orthogonal flanges, but of different size. FIG. 2g shows an Armstrong beveled grommet 44 with flanges of different tube body orientation. FIG. 2h shows a grommet 45 in which flange 30 is slightly larger than flange 28 so that risk of unintended explantation is minimized. However, flange 30 is thinner than flange 28 so that flange 30 is flexible to facilitate removal when desired. In order to further facilitate removal, flange 28 is provided with a tab 45a which can be grasped by forceps or a similar instrument.

Figure 3:
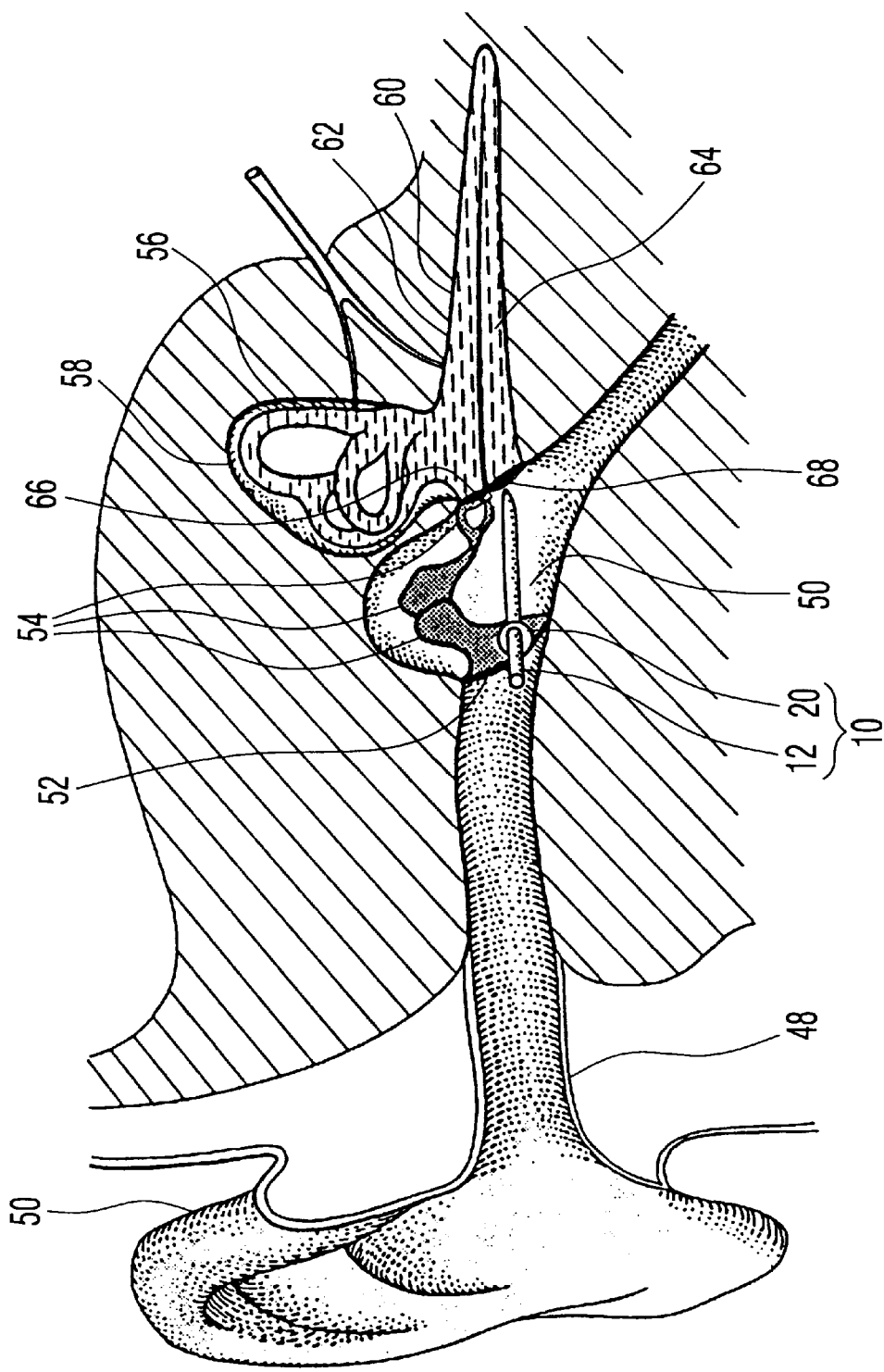
FIG. 3 shows a side view of the implant of FIG. 1 after implantation in an ear.

The implantation and use of implant 10 will now be described using the treatment of inner ear disease as an example. FIG. 3 shows a view of an ear with some anatomical structures omitted for simplicity. Outer ear 46 consists of the externally visible parts of the ear and external auditory meatus 48, a tube leading to middle ear 50. Middle ear 50 is an irregular space beyond tympanic membrane or eardrum 52 which contains ossicles 54.

Ossicles 54 provide mechanical linkage between eardrum 52 and inner ear 56. Inner ear 56 includes vestibule 58 and cochlea 60. Cochlea 60 is a tapered canal divided into a vestibular canal 62 and a tympanic canal 64. Both of these canals are connected to middle ear 50, by an oval window 66 and a round window 68, respectively. Both of these canals also contain perilymph or inner car fluid. It is the delivery of medicament to the inner ear fluid which is needed for direct treatment of inner ear disease. Specifically, as round window 68 has been found to be permeable to many substances, the medication is placed on round window 68 and allowed to permeate through round window 68 and into the inner ear fluid.

The implantation of implant 10 for treatment of inner car disease is a relatively straightforward procedure that can be done as an office procedure under local anesthesia. The first step is to make an opening in eardrum 52. Typically, a bloodless 2 mm opening in the posterior quadrant of eardrum 52 is made using a laser. A myringotomy knife can also be used to make the opening. If the physician cannot ascertain the location of round window 68, a smaller observation opening can be made in eardrum 52 in order to determine where the 2 mm opening should be made. An otoendoscope is introduced into middle ear 50 to observe round window 68. If there are any obstructions to round window 68, they are removed with a small micro pick so that the medication can directly reach round window 68. Tube 20 is inserted into the opening in eardrum 52. Although the exact geometry and size of tube 20 will be patient and procedure dependent, preferable tube sizes include an inside diameter of approximately 1.4 mm and a length of 2.2 mm. If grommet 45 (FIG. 2h) is used, flange 30 is preferably 3.25 mm in diameter and flange 28 is preferably 2.7 mm in diameter. Tube 20 facilitates insertion of wick 12 (especially larger diameter wicks) and tube 20 may reduce the incidence of unrepaired opening after wick 12 has been removed. After tube 20 and wick 12 are removed, the opening in eardrum 52 is repaired with a 3 mm rectangular piece of gelfilm impregnated with antibiotic ointment. This helps eardrum 52 to heal quickly. In the event that the opening in eardrum 52 does not heal after implant 10 is removed, eardrum 52 can usually be repaired with a minor office procedure using ear lope adipose tissue to close the opening. In all forty cases performed to date, the eardrum healed with the gelfilm patch.

Using direct visualization with the operating microscope, wick 12 is placed through tube 20 with distal end 14 in contact with round window 68 and proximal end 16 on the lateral side of eardrum 52. As previously mentioned, the diameter of wick 12 is preferably small enough with respect to the lumen of tube 20 so that distal end 14 of wick 12 can be observed through the lumen of tube 20 to help to ensure that distal end 14 is in contact with round window 68. If wick 12 is used with tube 20 and tube 20 has an inside diameter of 1.42 mm, wick 12 should be approximately 1 cm long and 0.75 mm in diameter. As any blood or other fluid will cause wick 12 to absorb the fluid and prematurely expand to prevent or hinder accurate placement of wick 12, it is important that the area around wick 12 remain dry while wick 12 is inserted. If there is too much fluid in the area, which occurs is around 10% of the cases, eardrum 52 is allowed to heal around tube 20 before wick 12 is implanted. A waiting period of approximately three to seven days between implantation of tube 20 and wick 12 ensures that eardrum 52 has healed and the area is dry. No anesthesia is typically needed if wick 12 is inserted at a later time.

In an alternative embodiment in which wick 12 is used alone without tube 20, the outer surface of wick 12 has a fluid impermeable coating or a fluid resistant coating which prevents absorption of fluids to hinder premature expansion if inadvertent fluid contact occurs. In this embodiment, wick 12 can be provided with an integral flange (or two flanges) to hold it in place in the eardrum.

In use, implant 10 remains in place for two to four weeks for most treatments. The patient inserts a dropper containing the medication into outer ear 46. When the medication contacts proximal end 16 of wick 12, wick 12 becomes saturated with the medication and the medication travels to distal end 14 under capillary action. As distal end 14 is in contact with round window 68, the medication permeates round window 68 and is absorbed into the inner ear fluids. Examples of medications that can be used with implant 10 include dilute Gentamicin otic solution (5–10 mg/cc three times daily for 2–3 weeks) for treatment of Meniere's disease and dexamethasone solution (24 mg/cc three times daily for several weeks) for treatment of sudden deafness or autoimmune ear disease.

As the medication can be delivered to the inner ear by the patient with a method similar to self-medicating eye disease using eye drops, there is no need for office visits for physician injections of medication. Unlike prior direct treatments of inner ear diseases, most of the medication is not lost down the eustachian tube when the patient swallows. Furthermore, because the medication is delivered directly to the inner ear, a high localized concentration of the medication is obtained. Finally, the implant according to the present invention, implantation procedure, and use of the implant are all cost and time effective.

Early clinical trials with implant 10 have been promising. In the six month prior to the filing of this application, forty patients have been treated for various conditions using implant 10 with excellent results. Implant 10 has remained in the middle ear for up to six weeks without adverse reaction or infection. Of the twenty-one patients with Meniere's disease who used implant 10 for self-treatment with dilute Gentamicin (5–10 mg/cc) otic solution, vertigo symptoms disappeared in 86% of the patients (at six month follow up). Approximately 77% achieved 100% reduced vestibular response as determined by bithermal caloric testing (mean 94%) and 56% achieved 100% reduced vestibular response as determined by ice-water caloric testing (mean 82%). Hearing was preserved in all but one patient, who failed to return for follow up visits, used the drops for over five weeks, and developed sudden deafness. Three patients (14%) had worse hearing from the treatment.

Three patients (14%) had a greater than 15 dB hearing improvement. In fifteen patients (72%), hearing was unchanged. Even the few patients who experienced increased loss of hearing were pleased with the results since vertigo was relieved. The clinical outcomes when implant 10 is used with dexamethasone solution have been more variable.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An otological implant for delivery of medicament from a first side of a membrane to a treatment site located on a second side of the membrane, the implant comprising a medicament-free wick having a distal end for contacting the treatment site, a proximal end for contacting a medicament source, and a body therebetween configured and dimensioned to pass through an aperture in the membrane and being made of a material capable of conveying the medicament from the proximal end to the distal end by capillary action.

2. The implant of claim 1 wherein the wick is made of polyvinyl acetate.

3. The implant of claim 1 wherein the wick has a substantially cylindrical shape.

4. The implant of claim 3 wherein the wick tapers toward the distal end.

5. The implant of claim 1 further comprising a tube member for supporting the wick configured and dimensioned to fit in the membrane aperture and having a first end for positioning on the first side of the membrane, a second end for positioning on the second side of the membrane, and a body therebetween having a lumen sized to receive the wick.

6. The implant of claim 5 wherein the tube member is made of titanium, a titanium alloy, stainless steel, nylon, or silicone.

7. The implant of claim 5 wherein the tube member length is shorter than the wick length.

8. An otological implant for delivery of medicament from a first side of a membrane to a treatment site located on a second side of the membrane, the implant comprising a wick having a distal end for contacting the treatment site, a proximal end for contacting a medicament source, and a body therebetween configured and dimensioned to pass through an aperture in the membrane and being made of a material capable of conveying the medicament from the proximal end to the distal end by capillary action; and a tube member for supporting the wick configured and dimensioned to fit in the membrane aperture and having a first end for positioning on the first side of the membrane, a second end for positioning on the second side of the membrane, and a body therebetween having a lumen sized to receive the wick;

wherein the first end of the tube member has a flange for preventing movement thereof.

9. The implant of claim 8 wherein the flange has a tab for facilitating removal of the implant.

10. The implant of claim 8 wherein the second end of the tube member has a flange for preventing movement thereof.

11. The implant of claim 8 wherein the flange is oriented at a non-orthogonal angle with respect to the tube member body.

12. The implant of claim 10 wherein at least one of the flanges is oriented at a non-orthogonal angle with respect to the tube member body.

13. The implant of claim 5 wherein the tube member body has a concave exterior surface.

\* \* \* \* \*